US012779086B2

(12) United States Patent
Um et al.

(10) Patent No.: US 12,779,086 B2
(45) Date of Patent: Nov. 3, 2026

(54) WOUND DRESSING COMPRISING HYALURONIC ACID-CALCIUM AND POLYLYSINE AND MANUFACTURING METHOD THEREFOR

(71) Applicant: YOUREH CO., LTD., Seoul (KR)

(72) Inventors: Hyang Mae Um, Seoul (KR); Ja Young Seol, Seoul (KR)

(73) Assignee: YOUREH CO., LTD., Seoul (KR)

(*) Notice: Subject to any disclaimer, the term of this patent is extended or adjusted under 35 U.S.C. 154(b) by 414 days.

(21) Appl. No.: 18/504,742

(22) Filed: Nov. 8, 2023

(65) Prior Publication Data

US 2024/0066179 A1 Feb. 29, 2024

Related U.S. Application Data

(62) Division of application No. 16/633,951, filed as application No. PCT/KR2018/008397 on Jul. 25, 2018, now abandoned.

(30) Foreign Application Priority Data

Jul. 26, 2017 (KR) ........................ 10-2017-0094693

(51) Int. Cl.

| | |
|---|---|
| ***A61L 26/00*** | (2006.01) |
| ***A61K 31/728*** | (2006.01) |
| ***A61K 31/785*** | (2006.01) |
| ***A61L 15/22*** | (2006.01) |
| ***A61L 15/42*** | (2006.01) |
| ***A61L 15/44*** | (2006.01) |
| ***A61L 15/64*** | (2006.01) |
| ***B29C 35/16*** | (2006.01) |
| ***B29K 105/04*** | (2006.01) |
| ***B29L 31/00*** | (2006.01) |

(52) U.S. Cl.

CPC ........ *A61L 26/0052* (2013.01); *A61K 31/728* (2013.01); *A61K 31/785* (2013.01); *A61L 15/225* (2013.01); *A61L 15/425* (2013.01); *A61L 15/44* (2013.01); *A61L 15/64* (2013.01); *A61L 26/0066* (2013.01); *A61L 26/009* (2013.01); *A61L 2300/236* (2013.01); *A61L 2300/252* (2013.01); *A61L 2300/404* (2013.01); *A61L 2300/418* (2013.01); *A61L 2300/424* (2013.01); *A61L 2400/04* (2013.01); *B29C 35/16* (2013.01); *B29K 2105/04* (2013.01); *B29L 2031/753* (2013.01)

(58) Field of Classification Search

CPC .. A61L 26/0052; A61L 15/225; A61L 15/425; A61L 15/44; A61L 15/64; A61L 26/0066; A61L 26/009; A61L 2300/236; A61L 2300/252; A61L 2300/404; A61L 2300/418; A61L 2300/424; A61L 2400/04; A61K 31/728; A61K 31/785; B29C 35/16; B29K 2105/04; B29L 2031/753

USPC .......................................................... 514/54

See application file for complete search history.

(56) References Cited

U.S. PATENT DOCUMENTS

| | | | | |
|---|---|---|---|---|
| 2005/0267068 | A1 | 12/2005 | Back et al. | |
| 2006/0094643 | A1 | 5/2006 | Svirkin et al. | |
| 2009/0042834 | A1 * | 2/2009 | Karageozian ........ | A61K 31/765 514/56 |
| 2016/0051723 | A1 | 2/2016 | Pomrink et al. | |
| 2016/0206773 | A1 | 7/2016 | Mousa et al. | |

FOREIGN PATENT DOCUMENTS

| | | | |
|---|---|---|---|
| CN | 102772821 | A | 11/2012 |
| CN | 104841008 | A | 8/2015 |
| CN | 106110377 | A | 11/2016 |
| JP | 2-268765 | A | 11/1990 |
| JP | 2005-514445 | A | 5/2005 |
| KR | 10-0721752 | B1 | 5/2007 |
| KR | 10-2017-0056423 | A | 5/2017 |
| WO | 03/059404 | A2 | 7/2003 |

OTHER PUBLICATIONS

Butergerds et al., "pH-Dependent Growth Laws and Viscoelastic Parameters of Poly-L-Lysine/Hyaluronic Acid Multilayers", Adv. Mater. Interfaces, 2017, 4: 1600592, 9 pages.

Nyman et al., "Hyaluronic acid, an important factor in the wound healing properties of amniotic fluid: In vitro studies of re-epithelialisation in human skin wounds", J Plast Surg Hand Surg, 2013, vol. 47, pp. 89-92.

Price et al., "The Role of Hyaluronic Acid in Wound Healing", Am J Clin Dermatol, 2005, vol. 6, No. 6, pp. 393-402.

* cited by examiner

*Primary Examiner* — Yih-Horng Shiao

(74) *Attorney, Agent, or Firm* — Vorys, Sater, Seymour and Pease LLP; Mih Suhn Koh

(57) ABSTRACT

The present invention relates to a wound dressing comprising hyaluronic acid-calcium and polylysine, and a manufacturing method therefor, the method comprising: (1) a step for adjusting each of the pH values of a hyaluronic acid-calcium salt and a polylysine aqueous solution to 8.4 or higher, and then mixing the hyaluronic acid-calcium salt and the polylysine aqueous solution to obtain a mixture liquid; and (2) obtaining a wound dressing from the mixture liquid obtained in Step (1).

11 Claims, 7 Drawing Sheets

HA-EDC-PLL

WOUND DRESSING COMPRISING HYALURONIC ACID-CALCIUM AND POLYLYSINE AND MANUFACTURING METHOD THEREFOR

CROSS-REFERENCE TO RELATED APPLICATIONS

This application is a divisional of U.S. patent application Ser. No. 16/633,951 filed on Jan. 24, 2020, which is a 371 of PCT/KR2018/008397 filed on Jul. 25, 2018, which claims priority to and the benefit of Korean Patent Application No. 10-2017-0094693 filed on Jul. 26, 2017, the disclosure of each of which is incorporated herein by reference in their entirety.

TECHNICAL FIELD

The present invention relates to a wound dressing comprising hyaluronic acid-calcium and polylysine, and a preparation method thereof.

BACKGROUND ART

Damage to blood vessels due to surgical procedures and physical injury causes bleeding. Mild surface bleeding eventually stops by the action of physiological hemostasis, a complex cascade between blood vessels, platelets and plasma factors. However, severe bleeding may require surgical and medical hemostatic means. In the surgical hemostasis, suturing of a ruptured blood vessel or an application of a hemostatic sponge or the like to an injured area can assist the surgical hemostasis. Hemostatic sponges or compositions are useful in surgery, vascular surgery, dental surgery and the like.

Previously-developed hemostatic products include sponge-type Tachocomb® Topical Thrombin which contains in vivo hemostatic coagulation factors and thereby can promote blood coagulation, and Surgicel®, Avitene®, ChitoClot® and the like, which absorb blood and thereby exhibit a blood-coagulation effect. Since Tachocomb® Topical Thrombin contains fibrinogen, thrombin, collagen and the like which are extracted from blood of cows or humans, it may cause a risk of infection and a hypersensitivity reaction during treatment. In addition, Surgicel®, Avitene® and ChitoClot® are disadvantageous in that blood coagulation performance and adhesiveness to an injured area are insufficient, and that the regeneration at the bleeding area is insignificant due to its low biocompatibility. Accordingly, various wound dressings have been developed for treating injured wounds having an excellent hemostatic performance.

Common external wound dressings used for wound healing of skin provide a moist environment suitable for healing, and should meet the requirements such as infection prevention, heat-retaining effect, prevention of adhesion between would surfaces, easiness of use, economic efficiency, absorptive property, moisture permeability, and the like. However, because wound dressings used for deep body cavity are applied to a wound area inside the living body, in addition to the common wound dressing requirements as described above, they must be hydrated in vivo to protect the wound during the wound healing period, but they must be naturally absorbed and removed after the healing is completed, so as not to affect normal tissues, and they also must have anti-adhesion functions.

Adhesion refers to a phenomenon that when the healing reaction continues for a long period of time during the healing process of injuries caused by inflammation, wounds, friction, surgery, etc., fibrous tissue is produced excessively, or blood is flowed out and coagulated, and thereby, the surrounding organs or tissues, which should be separated from each other, are adhered to each other. Such phenomenon may occur after all kinds of surgery. In general, it has been known that the incidence of long-term adhesion after surgery reaches 55% to 93%.

One of various methods for preventing adhesion is to use an anti-adhesive that forms a physical barrier during healing of tissue injury, so as to prevent the adhesion between adjacent tissues. Anti-adhesives can be broadly classified into two types in terms of their shape. The first is a film-type such as film, nonwoven fabric, sponge and the like, and the second is a solution-type such as gel. Previously-developed anti-adhesive products include Interguard, HyFence, Hibarry, GENTA Q, Medicurtain, Collatamp G, RegenPack, Guardix and the like. Conventional film-type anti-adhesives have an excellent adhesion inhibitory effect, but they have a limitation in that it is difficult to apply for a microscopic surgery using a laparoscope, the applicability of which has recently been expanded. Meanwhile, solution-type anti-adhesives are disadvantageous in that they are not easily adhered to the wounds due to exudates such as blood or the like which is appeared after surgery, and they may be removed together with the exudates or rapidly absorbed in the peritoneum. As a result, their role as a barrier for preventing adhesion does not last sufficiently.

In the most commonly used anti-adhesives, collagen and hyaluronic acid, which are biopolymers known as exhibiting excellent biocompatibility, are used as materials. However, since collagen is mostly extracted from the skin or muscle of cows or pigs, it has been reported that collagen proteins involved in immune responses can induce an immune response. In addition, cow-derived collagen has been reported as having safety issues due to the bovine spongiform encephalopathy (BSE) factor. Collagen extracted from other animals also carries the risk of animal virus infection. Hyaluronic acid has limitations in that when used alone, it decomposes relatively fast in the body, and diffuses and flows down the surface of a wound in a short time. In order to complement such properties of hyaluronic acid, a method for preparing a hyaluronic acid gel composition by crosslinking with BDDE, DVS, EDC/HoBt or the like has been proposed. However, a complicated process for removing the crosslinking agent is required, and the use of an additive such as carboxymethyl cellulose or the like may raise a safety issue due to its biodegradability.

Therefore, there is a need to develop a wound dressing that the disadvantages of the conventional wound dressings can be overcome, which is suitable to be applied to the living body, exhibits blood absorption, hemostatic and anti-adhesion effects, and can be used for effective healing not only external wounds but also wounds in the deep body cavity in a short time.

DETAILED DESCRIPTION OF THE INVENTION

Technical Problem

The present invention is to solve the technical problems of the prior art as described above, and thus provides a wound dressing, which can maintain its pores and support structure properly, can rapidly absorb blood, can exhibit a wound healing effect on surrounding tissues, is biodegradable so as to be applicable inside the human body, and can maximize hemostatic effect; and a preparation method thereof.

Technical Solution

In the present invention, the means for solving the technical problems as described above are as follows:

1. A wound dressing comprising hyaluronic acid-calcium and polylysine.

2. The wound dressing according to 1 above, comprising the hyaluronic acid-calcium and the polylysine in a ratio of 4:1 to 1:1.5 by weight.

3. The wound dressing according to 1 above, comprising the hyaluronic acid-calcium and the polylysine in a ratio of 2:1 to 4:3 by weight.

4. The wound dressing according to 1 above, comprising the hyaluronic acid-calcium and the polylysine in a ratio of 2:1 to 1:1.5 by weight.

5. The wound dressing according to 1 above, wherein the hyaluronic acid has a molecular weight of $2\times10^6$ to $3\times10^6$ Da.

6. The wound dressing according to 1 above, wherein the wound dressing is in the form of a liquid, foam or film.

7. A method for preparing a wound dressing according to any one of the above 1 to 6, comprising:

(1) mixing an aqueous hyaluronic acid-calcium salt, of which pH is adjusted to 8.4 or higher, with an aqueous polylysine, of which pH is adjusted to 8.4 or higher; and (2) obtaining a wound dressing from a mixed solution obtained in Step (1).

8. The method according to 7 above, wherein the pH values of the aqueous hyaluronic acid-calcium salt and the aqueous polylysine are respectively adjusted to a range of 8.4 to 9.0.

9. The method according to 7 above, wherein a liquid-type wound dressing is obtained in Step (2) from the obtained mixed solution.

10. The method according to 7 above, wherein the mixed solution is freeze-dried to obtain a foam-type wound dressing in Step (2).

11. The method of 7, wherein the mixed solution is applied onto a substrate or into a mold, and then dried to obtain a film-type wound in Step (2).

Advantageous Effects

According to the present invention, there is provided a liquid, foam and film-type wound dressings, comprising hyaluronic acid-calcium and polylysine; and a preparation method thereof.

In the present invention, a liquid, foam and film-type wound dressings capable of being applied to an internal and external wound areas in the body can be easily prepared from a mixed solution obtained by mixing an aqueous hyaluronic acid-calcium salt and an aqueous polylysine, pH of which are respectively adjusted to 8.4 or higher.

The wound dressing comprising hyaluronic acid-calcium and polylysine according to the present invention meets the requirements for a wound dressing for deep body cavity and can minimize a reaction caused by foreign substances because hyaluronic acid, a biologically derived material with no chemical crosslinking, is used, shows no residual toxicity, can be decomposed and absorbed after being retained in the body for a certain period of time, does not interfere with the wound healing process after surgery, and has an anti-adhesion performance that can be effective when applied to a surgical area. In addition, the use of calcium and polylysine can impart a superior hemostatic function, by which can inhibit the occurrence of tissue adhesion, likelihood of which may be increased due to coagulation following blood leakage. Further, the antimicrobial activity of polylysine results in inhibitory effect against wound infection. Thus, it was found that the wound dressing of the present invention could be distinguished from conventional products.

The liquid-type wound dressing of the present invention is advantageous in that it provides a hemostatic action by calcium and a wound healing effect by hyaluronic acid, and can be conveniently used according to properties of the formulation.

The foam-type wound dressing can maintain its pores and support structure properly, which allows rapid blood absorption, provides an adhesive force to tissues and promotes blood coagulation, so as to maximize hemostatic effect. It also exhibits a wound healing effect on surrounding tissues, and is biodegradable to be applicable in vivo to the human body. Further, the foam-type wound dressing has a smooth texture and an even surface, rapidly absorbs blood and exudate from the wound area, has an ability to fix the wound area, and shows excellent hemostatic performance. Thus it can be applied to various fields where wound infection inhibition and wound healing are needed.

In addition to the properties enumerated above, the film-type wound dressing can maintain its shape for a certain period of time under a wet condition, and thus can be useful in the protection and treatment of wound areas.

DETAILED DESCRIPTION OF THE EMBODIMENTS

Figure 1:
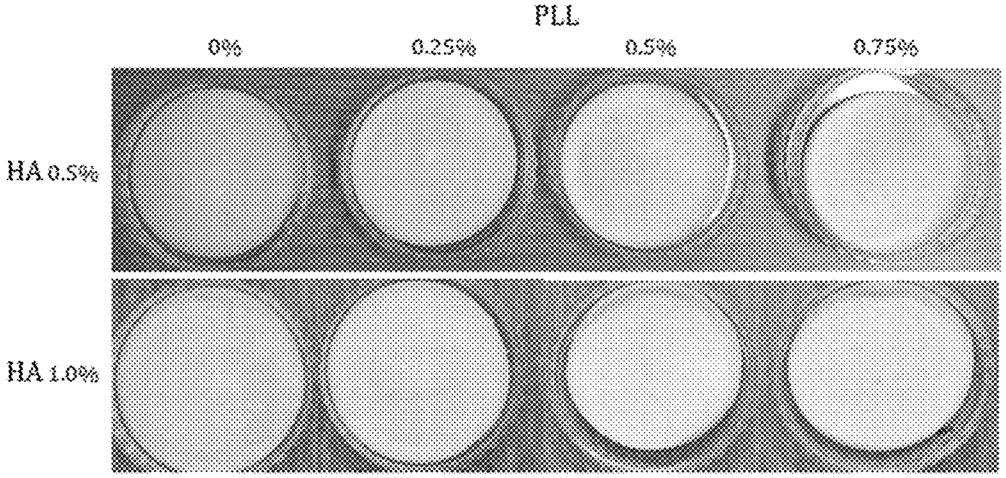
FIG. 1 is a result of observing the appearance of the pads comprising hyaluronic acid-calcium and polylysine prepared in Examples of the present invention, depending on the weight ratio between hyaluronic acid and polylysine.

Hyaluronic acid (hereinafter, also referred to as 'HA') is a long linear polysaccharide composed of β-D-glucuronic acid and β-D-N-acetylglucosamine, linked via alternating beta bonds each other, and is a biodegradable and biocompatible natural polymer widely found in nature with a broad range of molecular weight from 1,000 Da to 10,000,000 Da.

It has been known that hyaluronic acid is highly distributed in the vitreous body of the eye, joint fluids, cartilages and skin in the form of a highly viscous gel in which hyaluronic acid is combined with a large amount of water, and that it plays a role of lubricating joints, providing flexibility to the skin, and preventing bacteria from penetrating the skin with high viscosity. Therefore, until now, it has been used in various fields such as degenerative arthritis, cataracts, wrinkle improvement, drug delivery, stem cell support, cosmetic moisturization and the like. It is also present in a large amount in extracellular matrix of tissues so as to regulate differentiation and proliferation of cells, and its wound healing effect (Erika Nyman et al., J. Plast Surg Hand Surg. 2013; 47; 89-92) and wound healing mechanism (Richard D Price et al., Am J Clin Dermatol; 2005; 6 (6) 393-402) have been reported.

In recent studies, pharmacological actions have been reported, for which low-molecular weight hyaluronic acid can induce blood vessel regeneration of surrounding injured tissues, thereby effectively healing wounds. Based on such properties, hyaluronic acid has been widely used in the field of wound therapeutic agents, arthritis therapeutic agents, drug delivery systems and tissue engineering. In addition, due to the properties such as excellent biocompatibility, biodegradability and prevention of tissue adhesion, hyaluronic acid is also used itself as an anti-adhesion agent. However, it has been known that the conventional hyaluronic acid provided in the form of a sodium salt has no hemostatic action.

Polylysine (ε-Poly-L-lysine, hereinafter, also referred to as 'PLL') is composed of 25 to 35 L-lysine which is a strongly basic amino acid, and thus it has positive charge. The positively charged-polylysine can form an ionic bond with cell membrane of a microorganism having negative charge, by which it exhibits antimicrobial activity which inhibits proliferation of microorganism. Because of such properties, PLL has been widely used as a natural antimicrobial agent (natural preservatives, natural antiseptics, etc.) or natural food preservatives. Polylysine has a broad antimicrobial spectrum, showing antimicrobial activity against all bacteria (gram positive, gram negative, fungi), and is stable against pH changes, and thus, its antimicrobial activity is maintained without any significant fluctuation in a minimum inhibitory concentration (MIC) under a weakly acidic to a neutral pH (pH 4.0 to 8.0) region. Further, PLL is stable against heat, which results in no decrease in antibacterial activity due to heat. It has been also known that polylysine induces platelet aggregation, and that its ability to induce platelet aggregation depends on its molecular size.

Calcium has been known as a major factor in the treatment of wounds. It has been also known that calcium is essential for protein synthesis and collagenase activity together with magnesium, and that promotes coagulation to stop bleeding from wounds. It has been also known as a bio factor which promotes keratinocyte differentiation. Commercially available dressing utilizing the efficacy of calcium in wound healing contains calcium alginate.

In the present invention, sodium ion of hyaluronic acid-sodium salt, which has biocompatibility and a wound healing ability, is substituted with calcium ion so as to impart hemostatic effect to the hyaluronic acid, and then the resultant is mixed with poly-L-lysine (PLL), which has antimicrobial activity and a platelet aggregation ability, thereby providing a gel-type wound dressing in the form of a solution, which is easy to use, as well as a wound dressing in the form of a foam pad or film which can be adhered to a wound area found not only the outside but also the inside of the living body. Accordingly, it was found that the form-type pads and film-type dressings show biocompatibility, blood absorption and hemostasis effects, and anti-adhesion effect, and thus they can be applied for effective healing of wounds in the deep body cavity as well as of external wounds in a short period of time, by which the present invention was completed.

Thus, the present invention relates to a wound dressing comprising hyaluronic acid-calcium and polylysine (hereinafter, also referred to as 'HA-PLL' or 'HA-Ca-PLL').

In the present invention, the molecular weight of the hyaluronic acid is in a range suitable for being decomposed and removed in the body after it is applied to the deep body cavity and wound healing is completed, preferably in a range of $2\times10^6$ to $3\times10^6$ Da, which has been known as having proper in vivo half-life for acting as a physical barrier.

The wound dressing contains the hyaluronic acid-calcium and the polylysine in a ratio of 4:1 to 1:1.5 by weight, preferably in a ratio of 2:1 to 4:3 by weight, more preferably in a ratio of 2:1 to 1:1.5 by weight.

In the present invention, the mixing ratio between hyaluronic acid-calcium and poly-L-lysine (PLL) is adjusted to the range as defined above, so as to obtain a foam or film-type wound dressing which has a texture and strength suitable for a wound dressing, and of which optimum pores can be maintained, thereby being capable of maximizing blood absorption rate and hemostatic effect.

The wound dressing according to the present invention may be a liquid-type comprising the hyaluronic acid-calcium and the polylysine, and may preferably be an aqueous solution of the hyaluronic acid-calcium and the polylysine.

The present invention relates also to a method for preparing a wound dressing comprising hyaluronic acid-calcium and polylysine, the method comprising:

(1) mixing an aqueous hyaluronic acid-calcium salt, of which pH is adjusted to pH 8.4 or higher, with an aqueous polylysine, of which pH is adjusted to pH 8.4 or higher; and (2) obtaining a wound dressing from a mixed solution obtained in Step (1).

In Step (2), the mixed solution obtained can be used as a liquid-type wound dressing as it is. The mixed solution can be freeze-dried to obtain a foam or pad-type wound dressing. Otherwise, the mixed solution can be applied onto a substrate or poured into a mold and then dried, to obtain a film-type wound dressing.

Hyaluronic acid used in the present invention is a polymer having a very high molecular weight, and typical hyaluronic acid refers to a hyaluronic acid sodium salt. The hyaluronic acid-calcium salt used in Step (1) may be one in which the sodium ion is substituted with calcium ion, by adding an aqueous solution of a calcium salt to an aqueous solution of hyaluronic acid-sodium salt. Any method known in the art may be used to convert hyaluronic acid sodium salt to calcium salt. For example, in such a substitution, the concentration of the aqueous solution of hyaluronic acid may be in the range of 0.5 to 1.0% by weight, and the concentration of the aqueous solution of calcium salt solution may be used in the range of 0.1 to 0.2% by weight. The aqueous solution of hyaluronic acid and the aqueous solution of calcium salt are mixed, and a resulting mixed solution is stirred at room temperature to obtain a hyaluronic acid-calcium salt. The amount of the aqueous solution of calcium salt is sufficient in an amount to substitute sodium ion in the aqueous solution of hyaluronic acid with calcium ion, that is, 1 equiv. or more relative to the aqueous solution of hyaluronic acid. Calcium salts that can be used for such substitution may be, for example, an inorganic acid salt or an organic acid salt such as calcium chloride, calcium acetate and the like, but are not limited thereto, and any calcium salts of inorganic acid or organic acid known in the art may be used without any limitation.

In Step (1), the pH values of the aqueous solutions of hyaluronic acid-calcium salt and polylysine solution are respectively adjusted to 8.4 or higher, and then the aqueous solutions of hyaluronic acid-calcium salt and polylysine are mixed together to prepare a mixed solution.

In order to prepare a foam-type pad from hyaluronic acid, a freeze-drying process must be carried out. Herein, it has been known that it is difficult to make a pad have a uniform surface since the pad tends to become brittle or have a rough surface. In addition, when hyaluronic acid is mixed with poly-L-lysine, it is difficult to make into a foam-type because they do not disperse uniformly but rather entangle with each other to form a precipitate.

In the present invention, when mixing the hyaluronic acid-calcium salt and the poly-L-lysine, the pH value of the mixed solution is adjusted to a basic range, preferably pH 8.4 or higher, more preferably pH 8.4 to 9.0, so as to make the reactants not be precipitated, by which a uniform mixed solution is prepared. When the pH is under 8.4, the hyaluronic acid-calcium salt and poly-L-lysine do not mix uniformly and form a precipitate. When the pH range is over 9.0, it is possible to make into foam, but it may be unsafe for human body and thus undesirable for use in the human body.

Meanwhile, in case that the aqueous solution of hyaluronic acid and the aqueous solution of poly-L-lysine are combined without pH adjustment, precipitate is formed, and if the pH is adjusted after mixing to 8.4 or higher, the aqueous solutions of hyaluronic acid and the poly-L-lysine are mixed with each other. However, the already-formed precipitate prevents from formation of homogeneous mixture, which makes it difficult to prepare a foam pad having uniform microstructures. In the present invention, such problem can be avoided by adjusting the pH of hyaluronic acid-calcium salt to 8.4 or higher with a basic solution, followed by adding thereto an aqueous solution of poly-L-lysine of which pH is also adjusted to pH 8.4 or higher. As a basic solution for pH adjustment, an aqueous solution of NaOH, KOH, $NaHCO_3$ or the like may be used, but not limited thereto, and any one known in the art may be used.

In Step (2), a liquid-type wound dressing may be obtained by filling the mixed solution obtained in Step (1) in a prefilled syringe, or a foam-type wound dressing may be obtained by stabilizing the mixed solution of hyaluronic acid-calcium salt and poly-L-lysine at a refrigeration temperature, preferably at 0 to −4° C. for 6 to 10 hours, followed by preforming freeze-drying under a typical freeze-drying condition, for example, after freezing at −10 to −20° C. for 10 to 12 hours, freeze-drying for 48 to 60 hours. In addition, a film-type wound dressing may be obtained by applying the mixed solution onto a substrate or pouring the mixed solution into a mold, followed by drying at 40 to 60° C. for 12 to 16 hours.

EXAMPLES

Hereinafter, the present invention will be described in more detail by way of examples. However, the examples presented herein are given for illustrative purposes only, and it is not intended the scope of the invention to be limited to or by the examples.

Examples 1 to 6, and Comparative Examples 1 and 2: Preparation of Foam-Type Wound Dressing (Pad)

5 g of hyaluronic acid was added to 450 ml of purified water, and stirred for 2 hours. 1.1 g of $CaCl_2$ was dissolved in 50 ml of purified water and added to the solution of hyaluronic acid, and resulting mixture was stirred slowly at room temperature for 3 hours to form hyaluronic acid-calcium salt. Then, HA and PLL, of which pH values are respectively adjusted to pH 8.4, are mixed in the amounts shown in Table 1 to prepare mixed solutions with 10 ml each in total volume, and the solutions were stabilized at 0 to 4° C. for 6 to 10 hours, frozen at −10 to −20° C. for 10 to 12 hours, and then freeze-dried to prepare HA-PLL foam-type wound dressings (hereinafter, also referred to as 'HA-PLL pad' or 'HA-Ca-PLL pad'), and the formation of foam was observed. The results are shown in Table 1 below. In Table 1, Comparative Examples 1 and 2 are the pads prepared only with HA substituted with calcium salt without PLL.

TABLE 1

| Category | HA-Ca Content (%) | PLL Content (%) | Pad Formation |
|---|---|---|---|
| Example 1 | 0.05 g (0.5%) | 0.025 g (0.25%) | ○ |

TABLE 1-continued

| Category | HA-Ca Content (%) | PLL Content (%) | Pad Formation |
|---|---|---|---|
| Example 2 | 0.05 g (0.5%) | 0.05 g (0.5%) | ○ |
| Example 3 | 0.05 g (0.5%) | 0.075 g (0.75%) | ○ |
| Example 4 | 0.1 g (1%) | 0.025 g (0.25%) | ○ |
| Example 5 | 0.1 g (1%) | 0.05 g (0.5%) | ○ |
| Example 6 | 0.1 g (1%) | 0.075 g (0.75%) | ○ |
| Comparative Example 1 | 0.05 g (0.5%) | — | ○ |
| Comparative Example 2 | 0.1 g (1%) | — | ○ |

Example 7: Preparation of Liquid-Type Wound Dressing

Sodium chloride was added to the mixed solution having a composition of Example 2 such that its concentration was 0.8% and resulting solution was filled into a prefilled syringe to prepare a liquid-type wound dressing.

Example 8: Preparation of Film-Type Wound Dressing

The mixed solution having a composition of Example 2 was poured into a 10 cm×10 cm mold, and allowed to stand in a 40° C. incubator for 12 to 16 hours to prepare a film-type wound dressing.

FIG. 1 is a photographic image showing the appearances of the pads prepared from the compositions of Examples 1 to 6, and Comparative Examples 1 and 2. As shown in Table 1 and FIG. 1, the pads were formed well for the compositions of Examples 1 to 6. However, the higher the HA content, the harder the pad, and the pads tended to become harder even when the PLL content was increased. Meanwhile, when the PLL content exceeded 0.75% (w/v) or when the HA content exceeded 1% (w/v) in the solution, the degree of hardness was too high and the pad became brittle. Therefore, it was evaluated to be appropriate that the HA content did not exceed 1.0% and the PLL content did not exceed 0.75% when providing the wound dressing in a foam or film-type.

Figure 2:
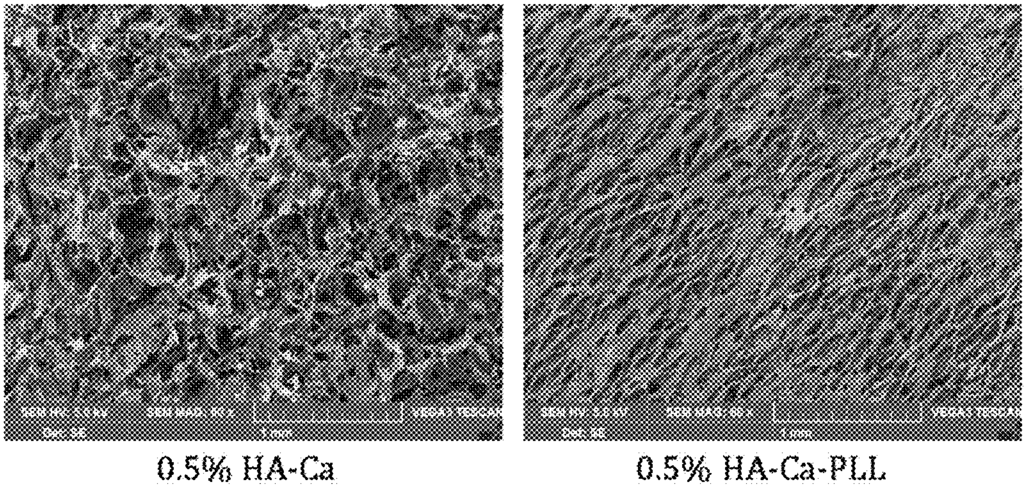
FIG. 2 shows high-resolution scanning microscope (transmission electron microscope, SEM) images of the pads comprising hyaluronic acid-calcium and polylysine according to Example 2 of the present invention and Comparative Example 1.

In order to identify the pore structure of the pad prepared from Example 2, which showed the highest hemostatic efficacy, and the pad prepared from Comparative Example 1, the pads were observed with a high-resolution scanning electronic microscope (transmission electron microscope, SEM), and the results are shown in FIG. 2. FIG. 2 shows that compared with the pad prepared only with 0.5% HA-Ca (i.e., HA-Ca content was 0.5% (w/v) based on the total volume of the preparation solution), the pores of the pad prepared by additionally mixing with 0.5% PLL (i.e., HA-Ca content was 0.5% (w/v) and PLL content was 0.5% (w/v) based on the total volume of the preparation solution) were denser.

Experimental Example 1: Measurement of Calcium (Ca) Content

The ratio of calcium substitution for the pads prepared from Examples 2 and 5, and Comparative Examples 1 and 2 were determined by Ca quantification using EDTA according to the following procedure:

About 0.1 g of the pad was taken, and dissolved in 25 mL of distilled water and 3 mL of buffer solution (pH 10.0), and then 6 drops of EBT indicator was added. The resulting solution was titrated with an EDTA reagent until red color changed to blue. The EDTA reagent was prepared by dissolving 0.3 g $Na_2H_2EDTA \times 2H_2O$ (which was dried at 80° C. for 1 hour and stored in a desiccator) in 250 mL of distilled water. The buffer solution (pH 10.0) was prepared by adding 17.5 g of $NH_4Cl$ to 142 mL of 28 wt % $NH_4OH$, and then adjusting the solution to be 250 mL in its final volume with double-distilled water. The EBT (Eriochrome black T indicator) reagent was prepared by dissolving 0.2 g of EBT in a mixture containing 15 mL of triethanolamine and 5 mL of ethanol (absolute). The mass and content (wt %) of calcium in the pads according to the mixed mass of hyaluronic acid-calcium and polylysine were calculated by the following Equations 1 and 2, and the results are shown in Table 2 below.

$$Ca \text{ mass} = \frac{0.306 \text{ g}}{250 \text{ mL}} \times EDTA \text{ volume} \times \frac{40.078 \text{ g/mol}}{292.24 \text{ g/mol}} \quad \text{Equation 1}$$

$$Ca \text{ content (wt \%)} = \frac{Ca \text{ mass}}{\text{Pad mass}} \times 100 \quad \text{Equation 2}$$

TABLE 2

| | Pad | Calcium Content (wt %) |
|---|---|---|
| Example 2 | 0.5% HA-0.5% PLL | 1.67 |
| Example 5 | 1% HA-0.5% PLL | 1.76 |
| Comparative Example 1 | 0.5% HA | 3.8 |
| Comparative Example 2 | 1% HA | 3.9 |

As shown in Table 2, when PLL was mixed, calcium content was decreased by 50% compared to the pad prepared only with HA.

Experimental Example 2: Evaluation of Blood Coagulation Property (Absorbance)

Blood and an anticoagulant (sodium citrate, 3.8 w/v %) in a ratio of 9:1 by volume were mixed in each test specimen in size of 1 cm×1 cm (width×length). 100 μl of a mixed solution was added dropwise, 10 μl of 0.2 M aqueous $CaCl_2$ was added, and then the blood was coagulated in an incubator at 37° C. for 10 minutes. Blood which did not participate in coagulation was eluted with 12.5 ml of distilled water. 1 ml of the eluate was taken to determine absorbance [AB] at 540 nm, and 1 ml of distilled water was taken to determine absorbance [AW] at 540 nm. In order to exclude the influence of distilled water contained in the blood eluate on absorbance, the blood coagulation property (absorbance) was calculated according to the following Equation 3.

$$\text{Absorbance} = \text{Absorbance of Blood Eluate}[AB] - \text{Absorbance of Distilled water}[AW] \quad \text{Equation 3}$$

In addition, the absorbance of the typical gauze (Comparative Example 3), and Algi Derm, (GnZ, Comparative Example 4) and RegenPack (Genewel, Comparative Example 5), which are commercially available wound dressings, was determined in the manner as described above. Algi Derm contains calcium alginate, and RegenPack is a foam-type wound dressing containing collagen. The absorbance of blood was determined in the same manner as above only with blood without any hemostatic dressing.

Figure 3:
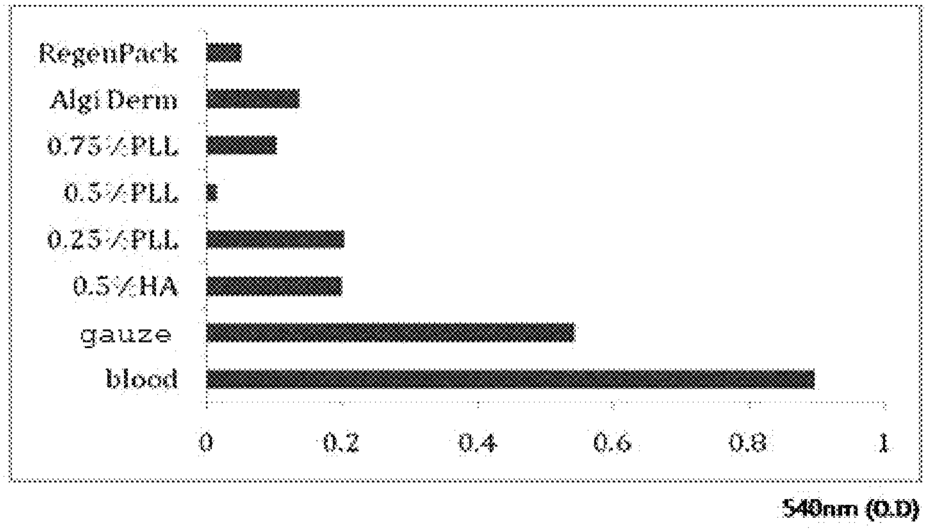
FIG. 3 is a graph showing results of evaluating blood coagulation properties of the pads (HA content of 0.5%) comprising hyaluronic acid-calcium and polylysine according to Examples of the present invention and Comparative Examples.
Figure 4:
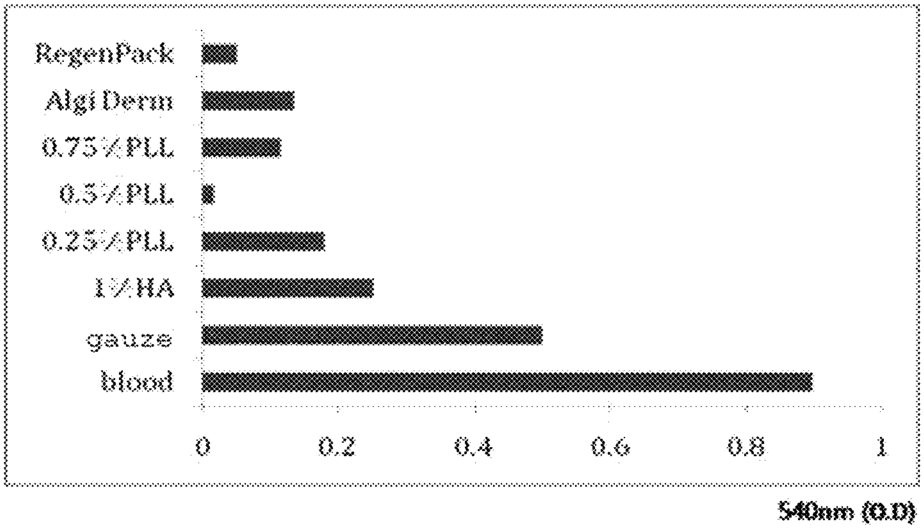
FIG. 4 is a graph showing results of evaluating blood coagulation properties of the pads (HA content of 1.0%) comprising hyaluronic acid-calcium and polylysine according to Examples of the present invention and Comparative Examples.
Figure 5:
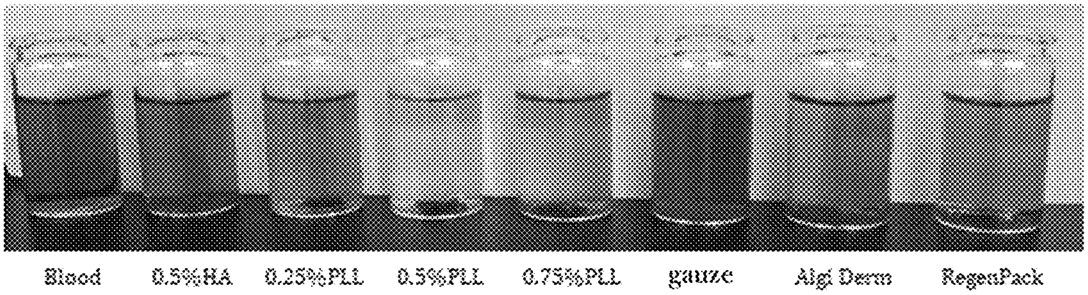
FIG. 5 is a photographic image showing results of evaluating blood coagulation properties of the pads comprising hyaluronic acid-calcium and polylysine according to Examples of the present invention and Comparative Examples.

The results of evaluating blood coagulation property of the HA-PLL foam-type pads according to the mixing ratio between HA and PLL are shown in Table 3, FIG. 3 (HA content of 0.5%) and FIG. 4 (HA content of 1.0%). FIG. 5 is a photographic image showing results of blood elution test for pure blood, pads containing 0.5% hyaluronic acid-calcium and polylysine-containing depending on their PLL contents, and Comparative Examples 1, and 3 to 5.

TABLE 3

| Category | HA-Ca | PLL | Blood Coagulation Efficacy Index* |
|---|---|---|---|
| Example 1 | 0.05 g (0.5%) | 0.025 g (0.25%) | 1.5 |
| Example 2 | 0.05 g (0.5%) | 0.05 g (0.5%) | 1 |
| Example 3 | 0.05 g (0.5%) | 0.075 g (0.75%) | 2 |
| Example 4 | 0.1 g (1%) | 0.025 g (0.25%) | 2 |
| Example 5 | 0.1 g (1%) | 0.05 g (0.5%) | 1 |
| Example 6 | 0.1 g (1%) | 0.075 g (0.75%) | 2 |
| Comparative Example 1 | 0.05 g (0.5%) | — | 2.2 |
| Comparative Example 2 | 0.1 g (1%) | — | 3 |
| | Product Name (Manufacturer) | Main Component | |
| Comparative Example 3 | Sterilized gauze (MediMedi) | Cotton Seed | 5 |
| Comparative Example 4 | Algi Derm (GnZ) | Calcium alginate | 2 |
| Comparative Example 5 | RegenPack (Genewel) | Collagen | 1 |

*Blood coagulation efficacy index was evaluated based on the results of evaluating blood coagulation property, i.e., absorbance (O.D.), according to the following criteria:
1: 0.1 or less; 2: greater than 0.1 and 0.2 or less; 3: greater than 0.2 and 0.25 or less, 4: greater than 0.25 and 0.3 or less; 5: 0.3 or more.

Experimental Example 3: Evaluation of Blood Coagulation Rate (Absorbance)

Figure 6:
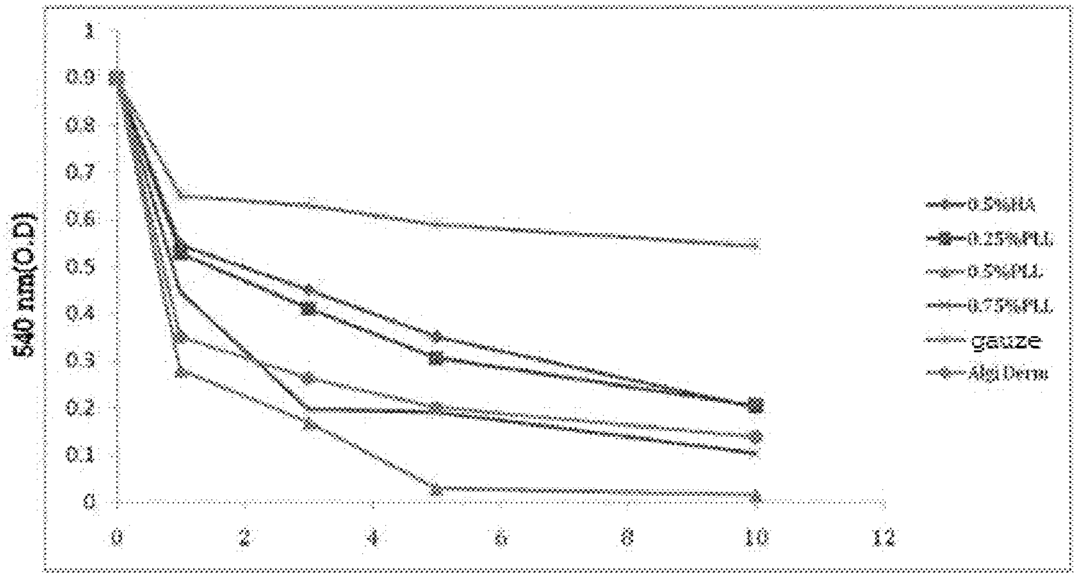
FIG. 6 is a graph showing results of evaluating blood coagulation properties of the pads (HA content of 0.5%) comprising hyaluronic acid-calcium and polylysine according to Examples of the present invention and Comparative Examples, depending on the coagulation time.
Figure 7:
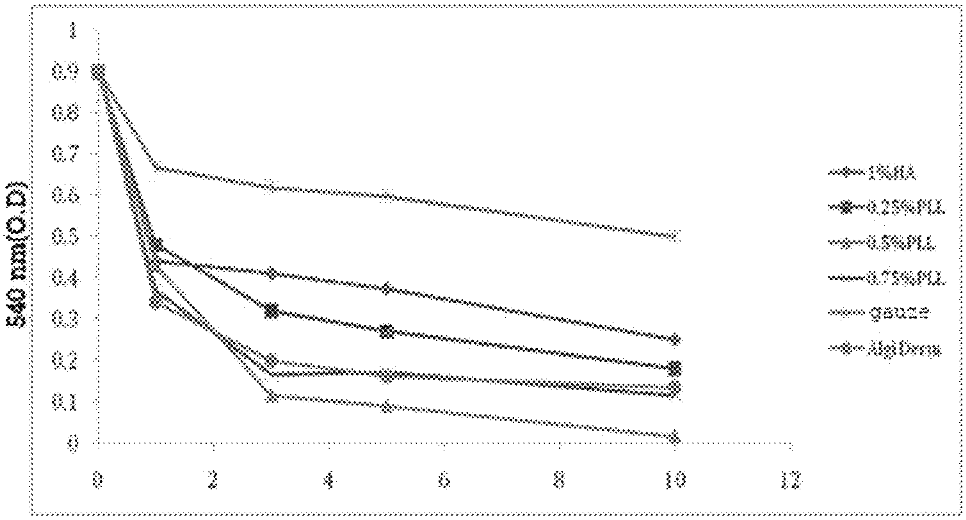
FIG. 7 is a graph showing results of evaluating blood coagulation properties of the pads (HA content of 1.0%) comprising hyaluronic acid-calcium and polylysine according to Examples of the present invention and Comparative Examples, depending on the coagulation time.

The blood coagulation rate was evaluated by measuring the absorbance of the blood eluate in the same manner as in Experimental Example 2, except that the blood coagulation times were 1, 2, 3, 5 and 10 minutes in a 37° C. incubator. The results are shown in FIGS. 6 and 7. FIGS. 6 and 7 are graphs showing the absorbance (O.D.) calculation results according to the PLL content when the HA content is 0.5% and 1.0%, respectively.

Experimental Example 4: Evaluation of Blood Absorption Rate

Figure 8:
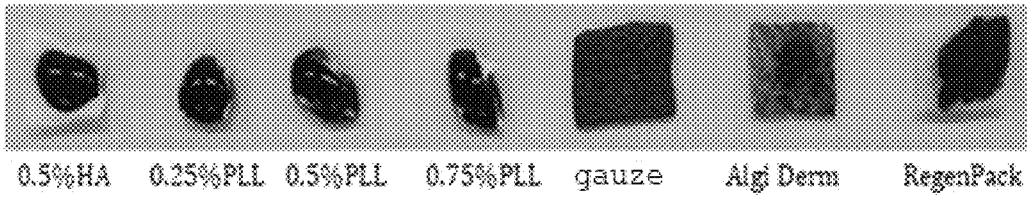
FIG. 8 is a photographic image showing the results when the blood is completely absorbed on the pads comprising hyaluronic acid-calcium and polylysine according to Examples of the present invention and on the specimens of Comparative Examples.

100 μl of blood was added dropwise onto 1 cm×1 cm (width×length) pad containing hyaluronic acid-calcium and polylysine, and then the time until the completion of blood absorption was observed so as to evaluate blood absorption rate, by which the suitability as a hemostatic pad was determined. Comparative experiments were carried out in the same manner for two commercially available products Algi Derm and RegenPack as controls. The results are shown in Table 4 and FIG. 8. FIG. 8 shows a photographic image taken within 5 seconds after addition of blood onto the foam-type pad with 0.5% HA content.

As shown in Table 4 and FIG. 8, the 1% HA-Ca and 0.5% HA-Ca pads showed a better hemostatic performance when PLL was mixed, and the hemostatic performance was the best when the PLL content was 0.5%. When the PLL content was 0.5% or more, the hemostatic performance was rather decreased. The 1% HA and 0.5% HA pads showed no difference in hemostatic performance, but the 0.5% HA pad showed a faster blood absorption rate. In view of cost, it was concluded that the 0.5% HA-containing pad would be better. Algi Derm and RegenPack both had excellent hemostatic performance, but the pads prepared in the Examples of the present invention showed a higher hemostatic performance than the commercially available products. RegenPack had disadvantage of having a low blood absorption rate.

TABLE 4

| Category | HA Content (%) | PLL Content (%) | Blood Absorption Rate Index* |
|---|---|---|---|
| Example 1 | 0.05 g (0.5%) | 0.025 g (0.25%) | 1.5 |
| Example 2 | 0.05 g (0.5%) | 0.05 g (0.5%) | 1 |
| Example 3 | 0.05 g (0.5%) | 0.075 g (0.75%) | 1 |
| Example 4 | 0.1 g (1%) | 0.025 g (0.25%) | 2 |
| Example 5 | 0.1 g (1%) | 0.05 g (0.5%) | 1.5 |
| Example 6 | 0.1 g (1%) | 0.075 g (0.75%) | 1.5 |
| Comparative Example 1 | 0.05 g (0.5%) | — | 3 |
| Comparative Example 2 | 0.1 g (1%) | — | 3 |
| | Product Name (Manufacturer) | Main Component | |
| Comparative Example 3 | Sterilized gauze (MediMedi) | Cotton Seed | 1 |
| Comparative Example 4 | Algi Derm (GnZ) | Calcium alginate | 1 |
| Comparative Example 5 | RegenPack (Genewel) | Collagen | 3 |

*Blood Absorption Rate index was evaluated based on the time until the completion of blood absorption according to the following criteria:
1: within 10 seconds; 2: within 30 seconds; 3: 1 minute or longer.

Experimental Example 5: Evaluation of Effect of Ca and PLL on Blood Coagulation Property In order to examine the effects of calcium and PLL on blood coagulation, foam-type pads respectively containing hyaluronic acid-calcium salt (HA-Ca), hyaluronic acid-sodium salt (HA-Na), hyaluronic acid-calcium and polylysine (HA-Ca-PLL), and hyaluronic acid-sodium and polylysine (HA-Na-PLL) were prepared in the same manner as in Examples, and the absorbances of the blood eluates were determined in the manner as described in Experimental Example 2. The results are shown in FIG. 9.

Figure 9:
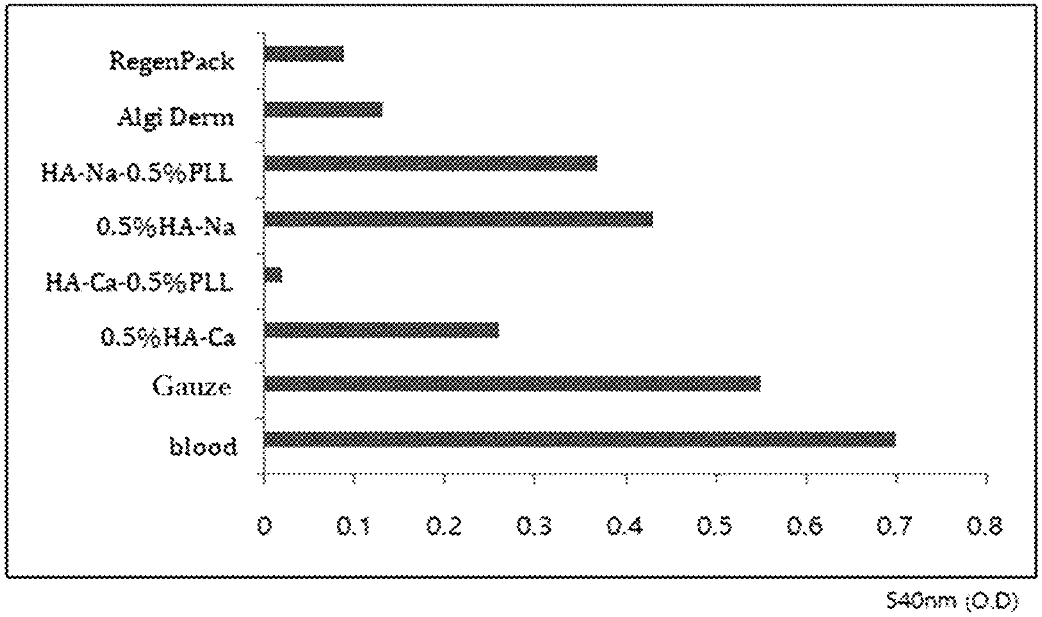
FIG. 9 is a graph showing hemostatic performances of pads respectively containing hyaluronic acid-calcium salt (HA-Ca), hyaluronic acid-sodium salt (HA-Na), hyaluronic acid-calcium and polylysine (HA-Ca-PLL), hyaluronic acid-sodium and polylysine (HA-Na-PLL), and Comparative Examples.

As shown in FIG. 9, the hyaluronic acid pad (HA-Na) without calcium substitution had no hemostatic performance, and the hyaluronic acid pad (HA-Ca) substituted only with calcium showed hemostatic performance. Therefore, it can be implied that calcium improved hemostatic performance. The pad (HA-Na-PLL) prepared by mixing only PLL without calcium substitution showed some hemostatic performance. The pad prepared from calcium-substituted hyaluronic acid also showed hemostatic performance, but the hemostatic performance was found to be higher when the pad was further mixed with PLL (HA-Ca-PLL). These results suggest that PLL also had an effect on hemostatic performance.

Figure 10:
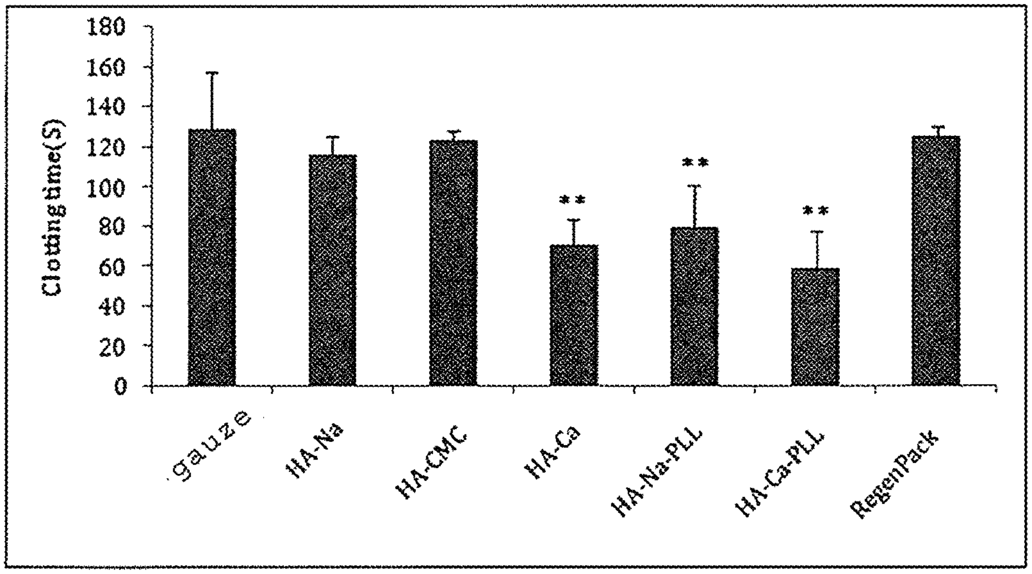
FIG. 10 is a graph showing results of evaluating hemostatic performances of pad respectively containing hyaluronic acid-calcium salt (HA-Ca)-, hyaluronic acid-sodium salt (HA-Na), hyaluronic acid-calcium and polylysine (HA-Ca-PLL), hyaluronic acid-sodium and polylysine (HA-Na-PLL), and Comparative Examples, for a portal injury model.

Experimental Example 6: Evaluation of Hemostatic Efficacy Using Portal Injury Model The hemostatic performance of the pads respectively containing hyaluronic acid-calcium salt (HA-Ca), hyaluronic acid-sodium salt (HA-Na), hyaluronic acid-calcium and polylysine (HA-Ca-PLL), and hyaluronic acid-sodium and polylysine (HA-Na-PLL) was evaluated by a method of portal injury model with mice. An anesthetized 8-week-old male mouse incised in the middle of the abdomen to view the portal vein. After puncturing the blood vessel with an 18 G needle, the bleeding site was covered with 1 cm×1 cm test specimen, and the time until the bleeding stopped (clotting time) was determined. An experiment was further performed for a pad (HA-CMC) prepared by mixing carboxymethyl cellulose (CMC) known as having a hemostatic action with hyaluronic acid-sodium salt as a Comparative Example. The results are shown in FIG. 10.

The results were consistent with those identified in Experimental Example 5. Hyaluronic acid without calcium substitution had no hemostatic performance, but hyaluronic acid substituted with only calcium showed a hemostatic performance. The pad prepared by mixing only PLL without calcium substitution also showed some hemostatic performance. The pad prepared using calcium-substituted hyaluronic acid also had hemostatic performance, but the hemostatic performance was found to be better when the pad was further mixed with PLL. Unexpectedly, the CMC-mixed pad showed no particular hemostatic performance, and RegenPack also had a low hemostatic performance compared to the pad of the present invention.

Experimental Example 7: Anti-Adhesion Test in Rat Cecal/Abdominal Wall Abrasion Model A rat cecal/abdominal wall abrasion model was used to evaluate the anti-adhesion performance of the wound dressings prepared in the above Examples. Five 7-week-old male Sprague-Dawley rats (SLC, Japan) were used per each group as experimental animals. In order to induce adhesion, the experimental animal was anesthetized by peritoneal administration of Ketamin.HCL (0.1 ml/100 g), its abdominal hair was removed, it was sterilized with 70% ethanol, and then a 4 to 5 cm incision was made on the midline at its abdomen. Subsequently, its caecum was taken out, and serous membrane of the cecum was rubbed with 1.2 cm×1.2 cm sterilized gauze until bleeding occurred, and the opposite peritoneum was injured in same size with a spatula. Two spots 1 cm away from the rubbing-injured areas were fixed with a 5-0 nylon suture to abut the two injured surfaces, thereby facilitating the formation of adhesion.

For a negative control group, physiological saline was added dropwise to the injured area, and for experimental groups, the wound dressings of Examples 1 to 3 and 8, and Comparative Examples 1, 4, and 5 were cut into 1 cm×1 cm in size and adhered to the injured area, or 1 ml of the liquid-type wound dressing of Example 7 was added dropwise to the injured area. Then, the peritoneum and skin were sutured. After the surgery, the animals were nurtured with a sufficient diet and water for one week, and then sacrificed. Using an adhesion evaluation system, scores obtained were summed and an average value was obtained (*Am. J. Obstet. Gynecol.,* 146, 88-92, 1983). The results are shown in Table 5 below. All results were expressed as a mean±standard error for each experimental group, and the significance of each group was tested in the level of $p<0.05$.

The degree of adhesion was evaluated according to the following criteria on a scale of 0 to 5 (0: No adhesion, 1: One thin film-like adhesion, 2: Two or more thin film-like adhesions, 3: Focal localized thick adhesions, 4: Plate-like localized adhesions, 5: Very thick adhesions with formation of blood vessels, or one or more plate-like dense adhesions).

The adhesion strength was evaluated according to the following criteria on a scale of 1 to 4 (1: Film-like adhesion which is easily released with very weak force, 2: Adhesion which requires moderate force to release the adhesion, 3: Adhesion which is released with application of considerable pressure, 4: Very strong adhesion which is difficult to be released or requires very high pressure to release the adhesion).

TABLE 5

| | Degree of Adhesion | Adhesion Strength | Adhesion Area($cm^2$) | Reduction ratio of Adhesion Area (%) |
|---|---|---|---|---|
| Negative Control | 3.73 ± 0.46 | 3.00 ± 0.00 | 0.80 ± 0.16 | 0 |
| Example 1 | 1.50 ± 1.08** | 1.25 ± 0.84** | 0.12 ± 0.12** | 85.0 |
| Example 2 | 1.40 ± 1.26** | 1.20 ± 0.84** | 0.07 ± 0.11** | 91.1 |
| Example 3 | 1.65 ± 1.15** | 1.30 ± 0.76** | 0.12 ± 0.08** | 85.0 |
| Example 7 | 1.87 ± 1.09** | 1.60 ± 0.75** | 0.26 ± 0.10** | 67.5 |
| Example 8 | 1.41 ± 1.15** | 1.15 ± 0.65** | 0.08 ± 0.15** | 90.0 |
| Comparative Example 1 | 1.75 ± 1.07** | 1.35 ± 0.84** | 0.16 ± 0.08** | 80.0 |
| Comparative Example 4 | 2.25 ± 1.50 | 1.50 ± 1.00* | 0.27 ± 0.18** | 62.5 |
| Comparative Example 5 | 1.75 ± 1.26* | 1.25 ± 0.96** | 0.26 ± 0.09** | 67.5 |

As shown in Table 5, the wound pad prepared only with hyaluronic acid without polylysine in Comparative Example 1 even showed a higher anti-adhesion effect, compared with Comparative Examples 4 and 5 which are commercially available wound pads. The tissue adhesion was significantly reduced in the experimental groups treated with the wound pads of Examples 1 to 3 of the present invention which were prepared with mixing polylysine at a concentration of 0.25%, 0.5% and 0.75%, respectively, compared with the control group. These results are consistent with the results obtained from the hemostatic efficacy test identified in the above Experimental Examples, and the anti-adhesion effect was the best when the polylysine was mixed at 0.5%. It was found that the liquid-type pad of Example 7 and the film-type pad of Example 8 were also effective in preventing adhesion.

Comparative Example 6: Preparation of Crosslinked HA-PLL Pad

In order to compare with the foam-type wound dressings comprising HA and PLL according to the present invention, a pad was prepared by crosslinking HA and PLL with a crosslinking agent.

1-ethyl-3-(3-dimethylaminopropyl)carbodiimide (EDC) was used as a crosslinking agent. The concentration of hyaluronic acid was 3% (w/v), and polylysine, the crosslinking agent (EDC), and hydroxybenzotriazole (HOBT) were added in equal molar amounts to the hyaluronic acid. Then, an aqueous NaOH was added in a molar ratio equal to HCl in PLL to neutralize the mixture. The mixture was uniformly mixed at 150 to 200 rpm at room temperature for 20 minutes. After mixing with a mechanical stirrer at 30° C. for 20 to 25 hours, 100 ml of 1% PBS solution was added to dilute the resulting mixture, and a cross-linked polymer, which was precipitated by adding ethanol, was filtered and freeze-dried to obtain the cross-linked HA-PLL. An aqueous solution of the cross-linked HA-PLL in 10 ml of distilled water was put into to a 60π plate and stabilized at 0 to 4° C. for 6 hours, and it was frozen −10 to −20° C. for 10 hours and then freeze-dried to prepare a pad. The photographic image of the thus-prepared pad is shown in FIG. 11.

Figure 11:
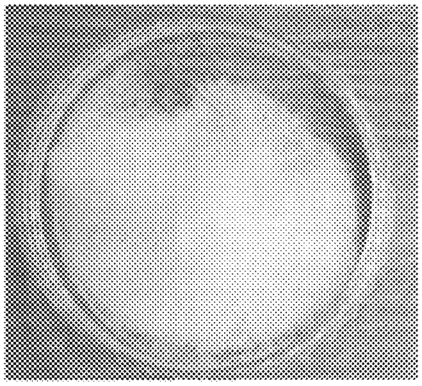
FIG. 11 is a photographic image of the appearance of the pad prepared by crosslinking hyaluronic acid with polylysine.
Figure 12:
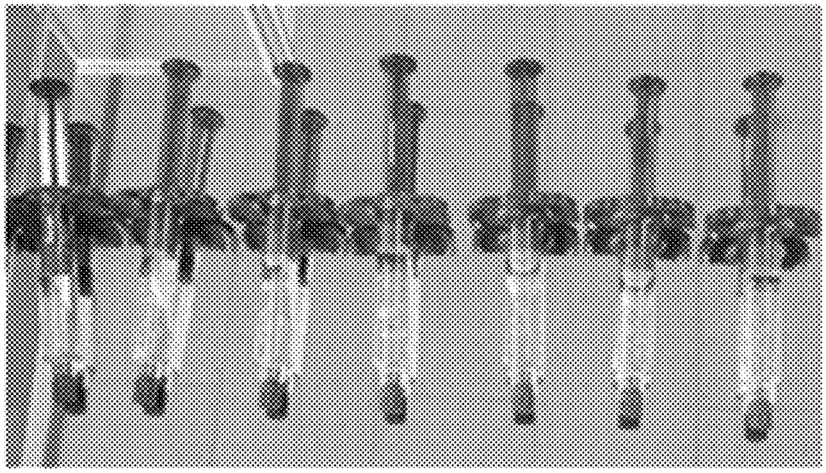
FIG. 12 is a photographic image of the appearance of prefilled syringes which are respectively filled with the liquid-type wound dressings comprising hyaluronic acid-calcium and polylysine according to Examples of the present invention.
Figure 13:
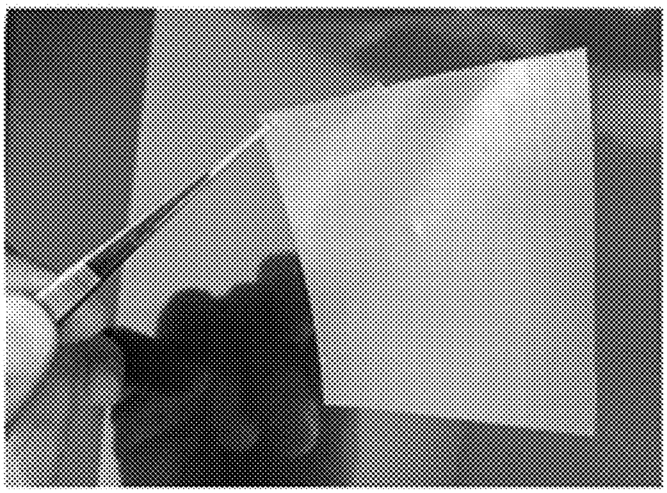
FIG. 13 is a photographic image of the appearance of the film-type wound dressing comprising hyaluronic acid-calcium and polylysine according to an Example of the present invention.

As shown in FIG. 11, in the mixture of HA-EDC-PLL, a uniform liquid was not formed, and it appears aggregation in aqueous phase. As a result, a pad-type wound dressing was not made.

While the present disclosure has been described above with reference to the particular illustrative embodiments, it will be understood by those skilled in the art to which the present disclosure pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

The invention claimed is:

1. A method for preparing a wound dressing, comprising:

(1) mixing an aqueous hyaluronic acid-calcium salt at pH 8.4 or higher and an aqueous polylysine at pH 8.4 or higher in the ratio of hyaluronic acid-calcium salt to polylysine of 4:1 to 1:1.5 by weight; and (2) forming a wound dressing from a mixed solution obtained in Step (1), wherein the wound dressing contains hyaluronic acid-calcium salt and polylysine which are not cross-linked.

2. The method according to claim 1, wherein pH of the aqueous hyaluronic acid-calcium salt and the aqueous polylysine is respectively adjusted to pH 8.4 or higher prior to mixing in Step (1).

3. The method according to claim 2, wherein pH of the aqueous hyaluronic acid-calcium salt and the aqueous polylysine is respectively adjusted to pH 8.4 to 9.0 prior to mixing in Step (1).

4. The method according to claim 1, wherein the wound dressing contains hyaluronic acid-calcium salt and polylysine which are not chemically cross-linked.

5. The method according to claim 1, wherein the wound dressing formed in Step (2) is in a liquid-, foam- or film-type.

6. The method according to claim 1, wherein the mixed solution obtained in Step (1) is filled into a prefilled syringe to form a liquid-type wound dressing in Step (2).

7. The method according to claim 1, wherein the mixed solution obtained in Step (1) is freeze-dried to form a foam-type wound dressing in Step (2).

8. The method according to claim 1, wherein the mixed solution obtained in Step (1) is applied onto a substrate or poured into a mold, and then dried to form a film-type wound dressing in Step (2).

9. The method according to claim 1, wherein the hyaluronic acid in the hyaluronic acid-calcium salt has a molecular weight of $2\times10^6$ to $3\times10^6$ Da.

10. The method according to claim 1, wherein the wound dressing does not contain a crosslinking agent.

11. The method according to claim 1, wherein the mixed solution obtained in Step (1) is a uniform solution containing hyaluronic acid-calcium salt and polylysine without precipitate.

* * * * *